United States Patent [19]

Wreford

[11] 4,450,112

[45] May 22, 1984

[54] PROCESS FOR CONVERTING NITRILES TO CARBOXYLIC ESTERS

[75] Inventor: Stanley S. Wreford, Wilmington, Del.

[73] Assignee: E. I. Du Pont de Nemours and Company, Wilmington, Del.

[21] Appl. No.: 325,028

[22] Filed: Nov. 25, 1981

[51] Int. Cl.$^3$ ................................................ C11C 3/02
[52] U.S. Cl. ............................ 260/410.9 R; 423/358; 560/94; 560/130; 560/215; 560/265
[58] Field of Search ............... 260/410.9 R, 410.9 L; 560/94, 215, 130, 265; 423/358

[56] References Cited

U.S. PATENT DOCUMENTS

| | | | |
|---|---|---|---|
| 2,666,782 | 1/1954 | Brockway | 560/215 |
| 2,816,135 | 12/1957 | Healy | 560/215 |
| 2,913,486 | 11/1959 | Veatch et al. | 260/486 |
| 2,921,088 | 1/1960 | Gasson et al. | 260/475 |
| 3,308,153 | 3/1967 | Matsuhisa | 260/475 |
| 3,313,844 | 4/1967 | Matsuhisa | 260/475 |
| 3,395,173 | 7/1968 | Oga et al. | 560/94 |
| 3,466,320 | 9/1969 | Hargis | 260/486 |
| 3,468,930 | 9/1969 | Pugach | 560/94 |
| 3,670,021 | 6/1972 | Goetz et al. | 260/361 R |
| 3,673,250 | 6/1972 | Rauch et al. | 260/561 N |
| 3,980,661 | 9/1976 | Smith et al. | 260/295.5 |
| 4,096,149 | 6/1978 | Feldman | 260/295.5 |

OTHER PUBLICATIONS

Villian et al., *Tetrahedron Letters*, 21, 2901 (1980).
Wainwright et al., CA, 92, 136021q.
Bennett et al., *J. Am. Chem. Soc.*, 95, 3030 (1973).
Bennett et al., *J. Am. Chem. Soc.*, 100, 1750 (1978).
Yoshida et al., *J. Am. Chem. Soc.*, 101, 2027 (1979).

*Primary Examiner*—Helen M. S. Sneed
*Attorney, Agent, or Firm*—James A. Costello

[57] ABSTRACT

Reaction of a nitrile, an alcohol and water in the presence of a catalyst comprising rhodium, iridium or platinum complexed with hydroxo and tertiary phosphine moieties, to produce the corresponding carboxylic ester.

15 Claims, No Drawings

PROCESS FOR CONVERTING NITRILES TO CARBOXYLIC ESTERS

BACKGROUND OF THE INVENTION

1. Field of the Invention

This invention relates to a catalytic process for the reaction of a nitrile with an alcohol and water to give the corresponding carboxylic ester and ammonia. No acid reactants are employed.

2. State of the Art

Catalytic processes that do not use acid reactants are known for the reaction of nitriles, alcohol and water to produce esters. The following are representative of this art: German OLS No. 2,832,760; U.S. Pat. No. 3,466,320; U.S. Pat. No. 3,308,153; U.S. Pat. No. 3,313,844; U.S. Pat. No. 2,913,486; and U.S. Pat. No. 2,921,088. None of these known processes, however, employs a catalyst described herein.

Catalytic processes that do not use acid reactants are known for the reaction of nitriles with water to produce the corresponding carboxamides. The following are representative of this art: Bennett, et al., *J. Am. Chem. Soc.*, 95, 3030 (1973) and ibid. 100, 1750 (1978); Yoshida, et al., *J. Am. Chem. Soc.*, 101, 2027 (1979); U.S. Pat. No. 3,670,021; U.S. Pat. No. 3,980,661; U.S. Pat. No. 3,673,250; U.S. Pat. No. 4,096,149; Villain, et al., *Tetrahedron Letters*, 21, 2901 (1980); and Wainwright, et al., CA, 92, 136021q. The first cited Bennett, et al. publication and U.S. Pat. No. 3,673,250 describe catalysts employed in the process of this invention. Neither of them, however, suggests use of such catalysts to produce esters rather than amides.

The Bennett publication, in column 2, page 3030, states that no hydrolysis of the amide to the acid was observed. Thus, Bennett does not suggest the instant process wherein reaction with a hydroxyl compound is the key process step, albeit to form an ester not an acid. U.S. Pat. No. 3,673,250 states at column 1, lines 16 and 17, that no by-products or almost no by-products are produced. Thus, the patent does not suggest the instant process which has high selectivity for carboxylic acid esters concerning which the patent is silent.

An important class of esters comprises methyl pentenoates made, by the process of this invention, from the corresponding pentenenitriles. Methyl 3-pentenoate and methyl 4-pentenoate can be converted via methoxycarbonylation by known techniques to dimethyl adipate. Dimethyl adipate is readily hydrolyzed to adipic acid which is used commercially in large volume in the preparation of condensation polymers, especially 66 nylon. Accordingly, an improved method for making methyl pentenoates would be of significant commercial importance.

Further, the pentenenitrile reactants are formed readily by the hydrocyanation of 1,3-butadiene. The nitrogen of the HCN used for hydrocyanating 1,3-butadiene comes from ammonia. For the production of methyl pentenoates from pentenenitriles to be most commercially viable, it is necessary that the by-product be ammonia and that the ammonia be readily available for recycle to produce more HCN. The process of this invention is particularly characterized in that ammonia is the by-product of the reaction to make ester, and furthermore, the ammonia is readily available for recycle to produce HCN.

In addition to methyl 3- and 4-pentenoates, esters of aliphatic monocarboxylic acids and dicarboxylic acids made by the process of this invention are useful as solvents, plasticizers, polymer intermediates, and starting materials for pharmaceuticals, agrichemicals, photographic chemicals, and many other articles of commerce.

SUMMARY OF THE INVENTION

The process of this invention comprises reacting a nitrile, an alcohol and water, in the presence of a catalyst selected from the group consisting of one or more of rhodium, iridium and platinum complexes with both hydroxo and phosphine moieties, to produce the corresponding carboxylic acid ester and recyclable ammonia.

The process of this invention proceeds by the following reaction:

$$RCN + H_2O + R'OH \xrightarrow{catalyst} RCOOR' + NH_3.$$

When the process is carried out in a closed system, the fact that the ammonia cannot escape places a thermodynamic upper limit of about 50% on ester selectivity. If the process is conducted with intermittent or continuous removal of ammonia, e.g., in a batch process with periodic venting or in a continuous process, the reaction can be driven to completion and ester selectivity can approach 100%.

In this description, percent ester selectivity is defined as 100%×(mols ester formed)/(mols nitrile charged—moles nitrile remaining). Amide and ammonia ($NH_3$) selectivities are defined correspondingly. The percent nitrile (RCN) conversion is defined as 100%×(mols nitrile charged—moles nitrile remaining)/(mols nitrile charged).

Preferred nitriles comprise from 2 to 18 carbons, most preferably from 2 to 12 carbons. Preferred nitriles include alkanenitriles of at least 2 carbons, alkanedinitriles of at least 3 carbons, alkenenitriles of at least 4 carbons, and alkenedinitriles of at least 6 carbons. Preferred alcohols are the primary and secondary lower alkanols of 1 to 8 carbon atoms.

The catalyst is a hydroxo compound (complex) of rhodium, iridium, or platinum, in which compound the metal is also bonded to a tertiary phosphine ligand. The catalyst can be added already formed into the reaction mixture, or, it can be added as a precursor in which the hydroxo moiety is formed in situ. It is preferred that the catalyst or catalyst precursor be soluble in the reaction mixture to the extent of at least about 0.01% under process conditions. In this description of the invention, the term "catalyst" is intended to include both catalysts and catalyst precursors which form catalysts under the reaction conditions of this invention.

Preferred catalysts include:

$Rh(OH)(CO)(P(C_6H_5)_3)_2$,
$RhCl(CO)(P(C_6H_5)_3)_2$,
$RhCl(P(C_6H_5)_3)_3$,
$Ir(OH)(CO)(P(C_6H_5)_3)_2$,
$Pt(P(C_2H_5)_3)_3$,
$(PtH(P(C_2H_5)_3)_3)OH$,

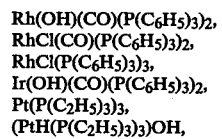

$Pt((C_6H_5)_2PCH_2CH_2COO)_2$, and

$Pt(Cl)_2((C_6H_5)_2PCH_2CH_2COOH)_2 + 2NaOH.$

Although the process can be operated at temperatures as low as 100° C., for practical rates it has been found that temperatures of about 125° C. to 250° C. are desirable. The preferred range of temperature is 150° C. to 200° C.

There are several characteristics of the process of this invention which distinguish it from processes of the prior art. The characterizing features include the following. This process produces esters in relatively high yield. This feature can be referred to as high selectivity for ester formation, or simply high ester selectivity. Ester formation of at least about 5% is the norm and selectivities above 10% or 20% are very typical. In a continuous operation wherein ammonia is removed as it is formed, ester selectivity will generally exceed about 50% and can approach 100%.

Another feature of this invention is that it gives ammonia as a by-products. The ammonia need not be removed from the reaction systems because it does not destroy the catalyst or inhibit the rate of reaction. However, if it is desired to improve ester selectivity above about 50%, the ammonia can be removed. In fact, the ammonia is readily recyclable to form HCN which can then be processed into starting nitriles in a continuous process.

Ammonia produced in the process of this invention can be recycled in a continuous process as follows. The ammonia is reacted with methane and oxygen to produce HCN which is reacted with the appropriate olefin, in the presence of a metal catalyst, to form the desired starting nitrile reactant. For example, esterification of 3-pentenenitrile yields methyl 3-pentenoate and ammonia. The ammonia can be converted to HCN as described above, and the HCN can be reacted with butadiene to form the 3-pentenenitrile starting reactant.

DETAILS OF THE INVENTION

In each of the starting nitriles and dinitriles employed in the process of this invention, the carbon bonded to a —CN group is also bonded to at least one hydrogen. In an alkenenitrile or an alkenedinitrile, any carbon that is doubly bonded to another carbon is separated from a —CN group by at least one carbon. Most preferably, the nitrile will contain from 2 to 6 carbons. Examples of operable nitriles are acetonitrile, propionitrile, butyronitrile, isobutyronitrile, hexanenitrile, 2-ethylhexanenitrile, dodecanenitrile, octadecanenitrile, 3-butenenitrile, 3-pentenenitrile, 4-pentenenitrile, undecylenonitrile, succinonitrile, α-methylglutaronitrile, adiponitrile(hexanedinitrile), 3-hexenedinitrile, sebaconitrile, and dodecanedinitrile.

Examples of primary and secondary lower alkanols are methanol, ethanol, 1-propanol, 2-propanol, 1-butanol, 1-methyl-1-butanol, 2-methyl-1-butanol, hexanol, and 2-ethylhexanol. Alkanols of 1 to 4 carbons are most preferred because of availability and ease of isolation of the product esters. Methanol is especially preferred, since it is the cheapest alcohol available, especially on a molar basis.

The stoichiometric amount of alkanol is one mol per equivalent of nitrile, and the process can be operated at this ratio. Usually, however, to insure maximum conversion and selectivity in a reasonable time at least 5 mols and preferably at least 10 mols of alkanol per equivalent of nitrile is used. The preferred range is about 10 to 20 mols of alkanol per equivalent of nitrile. Higher ratios can be used, but no advantage results.

The process of this invention will operate with only stoichiometric amounts of water. It is advantageous, however, to use an excess of water, at least about 2 mols per equivalent of nitrile and preferably between about 4 to 10 mols. Higher ratios can be used but no advantage results.

As noted heretofore, the catalyst can be formed outside the reaction mixture or can be formed in situ. In either event, the metal/hydroxo/phosphine complex is optionally bonded to one or more other ligands such as carbonyl.

The phosphine bonded to the metal in the catalyst can be a trihydrocarbylphosphine in which the hydrocarbyl groups are the same or different and are n-alkyl of up to about 8 carbons or aryl of 6 to 12 carbons. Preferably, because of availability, all three hydrocarbyl groups in a given phosphine are the same. Examples are trimethylphosphine, triethylphosphine, tripropylphosphine, tripentylphosphine, trioctylphosphine, diethyl(phenyl)phosphine, butyldiphenylphosphine, triphenylphosphine, trinaphthylphosphine, and tris(biphenylyl)phosphine. Especially preferred are triphenylphosphine and trialkylphosphines in which the alkyl groups contain up to 4 carbons each. In addition, the phosphine can have an alkyl group that bears a terminal carboxylate function. Each of these functions associates with the metal atom to form a chelate ring.

The amount of catalyst charged will depend primarily upon the amount of nitrile present, and the ratio of equivalents of nitrile to gram atoms of metal in the catalyst can vary widely. Usually, for efficient use of the catalyst, the ratio will be at least 25/1 up to 100/1 or even higher. Preferably, the ratio will be from about 25/1 to 200/1, and most preferably from about 40/1 to 100/1. The number of equivalents of a mononitrile will be the same as the number of mols; for a dinitrile the number of equivalents will be twice the number of mols.

EXAMPLES

The following Examples illustrate the process of this invention. Of them, Examples 6 and 22 represent preferred embodiments.

The compositions of product mixtures were determined by GLC (gas-liquid chromatography). Known weights of internal standards were added to the mixtures before the determinations were performed. Methods and conditions used in the various GLC determinations are summarized in Table 1. In most cases separate determinations were required for ammonia, ester, and amide.

TABLE 1

| | GLC ANALYSES | | |
|---|---|---|---|
| Components Analyzed For | Internal Standard | Column | Conditions[1] |
| Ammonia | Diethyl ether | 10' × ⅛" (3.0 m × 0.3 cm) 8% Polypropylenimine on Chromasorb ® | Isothermal, 100° |
| Propionitrile | Isopropanol | 10' × ⅛" | Isothermal, |

TABLE 1-continued

GLC ANALYSES

| Components Analyzed For | Internal Standard | Column | Conditions[1] |
|---|---|---|---|
| Methyl propionate | | (3.0 m × 0.3 cm) Porapak ® Q | 180° |
| Propionamide | o-Dichlorobenzene | 6' × ⅛" (1.8 m × 0.3 cm) 10% Carbowax ® 20 M on Chromosorb ® | Isothermal, 160° |
| Propionitrile Ethyl propionate | Tetrahydrofuran | 10' × ⅛" (3.0 m × 0.3 cm) Porapak ® Q | Isothermal, 180° |
| Propionitrile Isopropyl propionate | Diethyl ether | 6' × ⅛" (1.8 m × 0.3 cm) Porapak ® Q | 16 min at 130°, heat to 220° at 32°/min, hold at 220° for 16 min |
| Acetonitrile Methyl acetate Acetamide | Tetrahydrofuran | 10' × ⅛" (3.0 m × 0.3 cm) Porapak ® Q | 2 min at 150°, heat at 10°/min to 200°, hold for 32 min |
| n-Butyronitrile Methyl butyrate Butyramide | o-Dichlorobenzene | 10' × ¼" (3.0 m × 0.6 cm) 10% SP-1000 on Chromasorb ® | 8 min at 80° heat at 16°/min to 200° hold for 8 min |
| Isobutyronitrile Methyl isobutyrate Isobutyramide | o-Dichlorobenzene | 10' × ¼" (3.0 m × 0.6 cm) 10% SP-1000 on Chromasorb ® | 8 min at 80° heat at 16°/min to 200°, hold for 8 min |
| Adiponitrile Dimethyl adipate | o-Dichlorobenzene | 10' × ⅛" (3.0 m × 0.3 cm) 10% SP-1000 on Chromasorb ® | Heat from 100° at 8°/min to 230°, hold for 16 min |
| 3-Pentenenitrile Methyl 3-pentenoate | o-Dichlorobenzene | 10' × ⅛" (3.0 m × 0.3 cm) 10% SP-1000 on Chromasorb ® | 4 min at 100°, heat at 4°/min to 200°, hold for 8 min |

[1]Flow Rate 17.0 ml/min, temperatures °C.,

EXAMPLE 1

A 75-ml stainless-steel pressure vessel was charged with 25 ml of methanol (19.83 g, 619 mmol), 3 ml of propionitrile (2.32 g, 42 mmol), 1 ml of water (1.0 g, 56 mmol), and 0.70 g of trans-Ir(OH)(CO)[P($C_6H_5$)$_3$]$_2$ (0.92 mmol). The apparatus was sealed and heated in an oil bath at 150° C. for 2 hours. After cooling to room temperature the vessel was opened, treated with an internal standard and analyzed by GLC. The results are presented in Table 2.

Example 2 was carried out by essentially the method of Example 1, with variations as noted in Table 2. Examples 3 to 37 and the control experiment, Comparative Example A, were carried out by essentially the method of Example 1 except that a 30-ml reactor was used instead of a 75-ml reactor, to provide more uniform heating. Other variations in materials and conditions are given in Tables 2 and 3.

In Examples 4 and 9, the reported amounts of ester and amide exceed the sum of 100% because of limitations inherent in the analytical method.

TABLE 2

ESTERIFICATION OF PROPIONITRILE WITH METHANOL

| Ex. | Catalyst | Mole Ratios RCN/H₂O/MeOH/Cat | Temp °C. | Time hr | % RCN Conv | % Selectivity Ester | Amide | NH₃ |
|---|---|---|---|---|---|---|---|---|
| 1 | Ir(OH)(CO)(P(C₆H₅)₃)₂ | 46/61/673/1 | 150 | 2 | 42 | 6 | 85 | — |
| 2 | Ir(OH)(CO)(P(C₆H₅)₃)₂ | 46/61/673/1 | 150 | 4 | 58 | 28 | — | — |
| 3 | Ir(OH)(CO)(P(C₆H₅)₃)₂ | 42/56/742/1 | 150 | 2 | 40 | 23 | 61 | — |
| 4 | Ir(OH)(CO)(P(C₆H₅)₃)₂ | 42/56/742/1 | 175 | 2 | 45 | 45 | 66 | — |
| 5 | Ir(OH)(CO)(P(C₆H₅)₃)₂ | 42/56/742/1 | 200 | 2 | 55 | 35 | 26 | — |
| 6 | Ir(OH)(CO)(P(C₆H₅)₃)₂ | 42/56/742/1 | 175 | 4 | 67 | 51 | 27 | — |
| 7 | Ir(OH)(CO)(P(C₆H₅)₃)₂ | 42/56/742/1 | 175 | 8 | 77 | 35 | 28 | — |
| 8 | Ir(OH)(CO)(P(C₆H₅)₃)₂ | 42/56/742/1 | 175 | 44 | 96 | 37 | 1 | — |
| 9 | Ir(OH)(CO)(P(C₆H₅)₃)₂ | 42/276/644/1 | 175 | 2 | 92 | 28 | 78 | — |
| 10 | Ir(OH)(CO)(P(C₆H₅)₃)₂ | 42/276/644/1 | 100 | 2 | 17 | 10 | 76 | — |
| 11 | Ir(OH)(CO)(P(C₆H₅)₃)₂ | 42/276/644/1 | 175 | 2 | 66 | 15 | 79 | — |
| 12 | Same × P(C₆H₅)₃ | 42/276/644/1 | 175 | 2 | 78 | 19 | 72 | 23 |
| 13 | RhCl(CO)(P(C₆H₅)₃)₂ | 42/56/742/1 | 150 | 2 | 21 | 29 | 17 | — |
| 14 | Rh(OH)(CO)(P(C₆H₅)₃)₂ | 42/56/742/1 | 150 | 2 | 24 | 25 | 54 | — |
| 15 | RhCl(P(C₆H₅)₃)₃ | 42/56/742/1 | 150 | 2 | 20 | 26 | 26 | — |
| 16 | RhCl(CO)(P(C₆H₅)₃)₂ | 42/276/644/1 | 175 | 2 | 28 | 43 | 52 | — |
| 17 | RhCl(P(C₆H₅)₃)₃ | 42/276/644/1 | 175 | 2 | 40 | 33 | 27 | — |
| 18 | PtCl₂((C₆H₅)₂PC₂H₄CO₂H)₂ + 2NaOH | 42/276/744/1 | 170 | 4 | 58 | 22 | 62 | — |
| 19 | Pt(P(C₂H₅)₃)₃ | 42/276/644/1 | 175 | 2 | 67 | 12 | 61 | 10 |
| 20 | Pt(P(C₂H₅)₃)₃ | 42/276/644/1 | 175 | 4 | 84 | 19 | 72 | — |

TABLE 2-continued

ESTERIFICATION OF PROPIONITRILE WITH METHANOL

| Ex. | Catalyst | Mole Ratios RCN/H2O/MeOH/Cat | Temp °C. | Time hr | % RCN Conv | % Selectivity Ester | Amide | NH3 |
|---|---|---|---|---|---|---|---|---|
| 21 | Pt(P(C2H5)3)3 | 42/276/644/1 | 175 | 6 | 90 | 26 | 57 | — |
| 22 | Pt(P(C2H5)3)3 | 42/276/644/1 | 175 | 24 | 98 | 55 | 37 | 22 |
| 23 | Pt(P(C2H5)3)3 | 42/276/644/1 | 175 | 36 | 100 | 52 | 23 | 31 |
| 24 | Pt(P(C2H5)3)3 | 42/276/744/1 | 175 | 48 | 100 | 52 | 16 | — |
| 25 | Pt(P(C2H5)3)3 | 42/276/644/1 | 150 | 4 | 63 | 10 | 72 | 12 |
| 26 | Pt(P(C2H5)3)3 | 42/111/716/1 | 175 | 4 | 63 | 40 | 43 | 20 |
| 27 | Pt(P(C2H5)3)3 | 42/166/693/1 | 175 | 4 | 56 | 21 | 73 | 19 |
| A | None | 42/276/744/0 | 175 | 4 | 6 | 0 | 2 | — |

TABLE 3

ESTERIFICATION OF NITRILES CATALYZED BY Pt(PEt3)3 (CHARGED) WITH METHANOL AND OTHER ALCOHOLS

| Ex. | Mole Ratios RCN/H2O/MeOH/Cat | RCN | R'OH | Temp °C. | Time hr | % RCN Conv | % Selectivity Ester | Amide | NH3 |
|---|---|---|---|---|---|---|---|---|---|
| 28 | 42/276/514/1 | Propionitrile | Ethanol | 170 | 24 | 98 | 8 | 85 | 3 |
| 29 | 42/276/744/1 | Propionitrile | Isopropanol | 175 | 4 | 100 | 20 | 46 | 3 |
| 30 | 42/276/744/1 | Propionitrile | Isopropanol | 175 | 24 | 100 | 21 | 21 | 11 |
| 31 | 42/276/744/1 | Acetonitrile | Methanol | 175 | 4 | 79 | 24 | 71 | 64 |
| 32 | 42/276/744/1 | Butyronitrile | Methanol | 175 | 4 | 62 | 6 | 64 | 8 |
| 33 | 42/276/744/1 | Butyronitrile | Methanol | 175 | 24 | 90 | 20 | 57 | 27 |
| 34 | 42/276/744/1 | Isobutyronitrile | Methanol | 175 | 4 | 60 | 12 | 80 | 17 |
| 35 | 42/276/744/1 | Isobutyronitrile | Methanol | 175 | 24 | 87 | 22 | 63 | 21 |
| 36 | 21/276/744/1 | Adiponitrile | Methanol | 175 | 48 | 99 | 22 | — | 30 |
| 37 | 42/276/744/1 | 3-Pentenenitrile | Methanol | 170 | 4 | 99 | 13 | — | — |

COMPARATIVE EXAMPLES B AND C

These Examples, summarized in Table 4, show that a compound which catalyzes hydration of a nitrile to the amide does not necessarily catalyze alcoholysis of a nitrile to the corresponding carboxylic acid ester to any practical extent. The catalyst employed in Examples B and C is Pd(OH)2(2,2'-bipyridine)H2O described by Villain, et al. in *Tetrahedron Letters,* 21, 2901 (1980), referred to in the "State of the Art" Section, supra. RCN is propionitrile in Table 4.

TABLE 4

| Ex. | Catalyst | Mole Ratios RCN/H2O/MeOH/Cat | Temp °C. | Time hr | % RCN Conv | % Selectivity Ester | Amide | NH3 |
|---|---|---|---|---|---|---|---|---|
| B | Pd(OH)2(bipyridyl) | 25/25/350/1 | 150 | 12 | Trace | Trace | — | — |
| C | Pd(OH)2(bipyridyl) | 21/28/309/1 | 100 | 2 | 41 | 1 | — | — |

I claim:

1. A process for making carboxylic acid esters and recyclable ammonia comprising reacting a nitrile of 2 to 18 carbons, an alcohol and water in the presence of a catalyst selected from the group consisting of one or more complexes of a metal with hydroxo and tertiary phosphine moieties, at a temperature between about 100° C. to 250° C., wherein the metal is selected from the group consisting of rhodium, iridium and platinum, and wherein the nitrile is selected from the group consisting of alkanenitriles of at least two carbons, alkanedinitriles of at least 3 carbons, alkenenitriles of at least 4 carbons, and alkenedinitriles of at least 6 carbons.

2. A process according to claim 1:

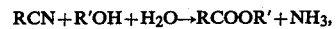

wherein R comprises 2 to 18 carbon atoms and R' comprises 1 to 8 carbon atoms.

3. A process according to claim 2 wherein R comprises 2 to 12 carbon atoms and R' comprises 1 to 4 carbon atoms.

4. A process according to claim 3 conducted at 150° to 200° C.

5. A process according to claim 1 wherein the alcohol is present in the amount of at least 5 mols per equivalent of nitrile reactant, water is present in the amount of at least 2 mols per equivalent of nitrile, and the ratio of nitrile to gram atoms of metal in the catalyst is at least about 25 to 1.

6. A process according to claim 5 wherein the alcohol is present in the amount of about 10 to 20 mols per equivalent of nitrile, water is present in the amount of about 4 to 10 mols per equivalent of nitrile, and the ratio of nitrile to gram atoms of metal in the catalyst is about 40 to 1 to 100 to 1.

7. A process according to claim 5 wherein ester selectivity exceeds about 10%.

8. A process according to claim 7 wherein ester selectivity exceeds about 50%.

9. A process according to claim 3 wherein the catalyst complex is soluble in the reaction mixture to the extent of at least about 0.01% under process conditions, said complex containing a phosphine moiety which is a trihydrocarbylphosphine wherein said hydrocarbyl groups are selected from alkyl of up to 8 carbons and aryl of 6 to 12 carbons.

10. A process according to claim 9 wherein the alcohol is present in the amount of about 10 to 20 mols per equivalent of nitrile, the water is present in the amount of about 4 to 10 mols per equivalent of nitrile and the ratio of nitrile to gram atoms of metal in the catalyst is about 40 to 1 to 100 to 1.

11. A process according to claim 10 wherein ester selectivity exceeds about 20%.

12. A process according to claim 11 wherein ester selectivity exceeds about 50%, comprising recycling ammonia and reacting the recycled ammonia with methane and oxygen to produce HCN and reacting the HCN with an olefin in the presence of a metal catalyst to produce starting nitrile.

13. A process according to claim 11 or 12 wherein the catalyst is trans-$Ir(CO)(OH)(P(C_6H_5)_3)_2$.

14. A process according to claim 11 or 12 wherein the catalyst is $Pt(P(C_2H_5)_3)_3$.

15. A process according to any one of claims 1 to 12 wherein the catalyst is selected from one or more of:

$Rh(OH)(CO)(P(C_6H_5)_3)_2$,
$RhCl(CO)(P(C_6H_5)_3)_2$,
$RhCl(P(C_6H_5)_3)_3$,
$Ir(OH)(CO)(P(C_6H_5)_3)_2$,
$Pt(P(C_2H_5)_3)_3$,
$(PtH(P(C_2H_5)_3)_3)OH$, $\overline{Pt((C_6H_5)_2PCH_2CH_2COO)_2}$, and $Pt(Cl)_2((C_6H_5)_2PCH_2CH_2COOH)_2 + 2NaOH$.

* * * * *